(12) United States Patent
Nordström et al.

(10) Patent No.: US 11,351,396 B2
(45) Date of Patent: Jun. 7, 2022

(54) METHODS FOR INVERSE PLANNING

(71) Applicant: ELEKTA INSTRUMENT AB, Stockholm (SE)

(72) Inventors: Håkan Nordström, Sollentuna (SE); Stella Riad, Sundbyberg (SE); Jens Sjölund, Sundbyberg (SE)

(73) Assignee: ELEKTA INSTRUMENT AB, Stockholm (SE)

( * ) Notice: Subject to any disclaimer, the term of this patent is extended or adjusted under 35 U.S.C. 154(b) by 81 days.

(21) Appl. No.: 16/282,054

(22) Filed: Feb. 21, 2019

(65) Prior Publication Data

US 2019/0255354 A1 Aug. 22, 2019

Related U.S. Application Data

(60) Provisional application No. 62/633,418, filed on Feb. 21, 2018.

(51) Int. Cl.
*A61N 5/10* (2006.01)
*G16H 20/40* (2018.01)

(52) U.S. Cl.
CPC ......... *A61N 5/1031* (2013.01); *A61N 5/1036* (2013.01); *A61N 5/1039* (2013.01);
(Continued)

(58) Field of Classification Search
CPC .......... A61N 2005/1041; A61N 5/1001; A61N 5/1031; A61N 5/1036; A61N 5/1039;
(Continued)

(56) References Cited

U.S. PATENT DOCUMENTS 5,373,844 A * 12/1994 Smith ................. A61N 5/1031
378/65
6,201,988 B1 * 3/2001 Bourland ............ A61N 5/1031
378/65
(Continued)

FOREIGN PATENT DOCUMENTS

CN 101410910 A 4/2009
CN 107708806 A1 2/2018

OTHER PUBLICATIONS

Chinee Office Action for Chinese Application No. 201910136086.3, dated Jan. 29, 2022, with English translation.
(Continued)

*Primary Examiner* — Dani Fox
*Assistant Examiner* — Soorena Kefayati
(74) *Attorney, Agent, or Firm* — Birch, Stewart, Kolasch & Birch, LLP

(57) ABSTRACT

Methods for dose or treatment planning for a radiotherapy system including a radiotherapy unit are provided. A spatial dose delivered can be changed by adjusting beam shape settings, and the delivered radiation is determined using an optimization problem that steers the delivered radiation according to objectives reflecting criteria for regions of interest including at least one of: targets to be treated during treatment of the patient, organs at risk and/or healthy tissue. The method includes determining an inner set of voxels and providing a first frame description for the inner set of voxels, where the first frame description reflects criteria for the inner set of voxels. Determining an outer set of voxels encompassing the target volume and the inner set of voxels and a frame description for the outer set of voxels is provided where each reflecting criteria for the outer set of voxels. The frame descriptions are then used in the optimization problem that steers the delivered radiation.

21 Claims, 8 Drawing Sheets

(52) U.S. Cl.
CPC ........... *A61N 5/1084* (2013.01); *G16H 20/40* (2018.01); *A61N 5/1001* (2013.01); *A61N 5/1081* (2013.01); *A61N 2005/1041* (2013.01)

(58) Field of Classification Search
CPC .. A61N 5/1081; A61N 5/1084; A61N 5/1041; G16H 20/40
See application file for complete search history.

(56) References Cited

U.S. PATENT DOCUMENTS

| | | | |
|---|---|---|---|
| 2003/0219098 A1* | 11/2003 | McNutt | A61N 5/1031 378/65 |
| 2004/0001569 A1* | 1/2004 | Luo | A61N 5/1031 378/65 |
| 2008/0011945 A1* | 1/2008 | Maurer | G21K 1/046 250/252.1 |
| 2008/0013687 A1* | 1/2008 | Maurer | A61N 5/1042 378/145 |
| 2008/0123813 A1* | 5/2008 | Maurer | G21K 1/046 378/96 |
| 2010/0104068 A1* | 4/2010 | Kilby | A61N 5/1031 378/65 |
| 2012/0123184 A1* | 5/2012 | Otto | A61N 5/1067 600/1 |
| 2012/0264996 A1* | 10/2012 | Chen | A61N 5/103 600/1 |
| 2012/0316377 A1* | 12/2012 | Danielsson | A61N 5/103 600/1 |
| 2014/0350322 A1* | 11/2014 | Schulte | A61N 5/1031 600/1 |
| 2015/0217135 A1* | 8/2015 | Bohsung | A61N 5/103 250/492.3 |
| 2016/0279444 A1* | 9/2016 | Schlosser | A61N 5/1071 |
| 2016/0303398 A1* | 10/2016 | Eriksson | A61N 5/1031 |
| 2017/0072220 A1* | 3/2017 | Zankowski | A61N 5/1031 |
| 2017/0119340 A1* | 5/2017 | Nakai | A61B 6/5205 |
| 2017/0209712 A1* | 7/2017 | H rdemark | A61N 5/1031 |
| 2017/0340900 A1* | 11/2017 | Moore | G16H 50/50 |
| 2018/0078792 A1* | 3/2018 | Ollila | A61N 5/1031 |
| 2018/0154177 A1* | 6/2018 | Bzdusek | A61N 5/1039 |
| 2019/0001154 A1* | 1/2019 | Vortman | A61N 5/1049 |
| 2019/0054315 A1* | 2/2019 | Isola | A61N 5/1038 |
| 2019/0054320 A1* | 2/2019 | Owens | A61N 5/1071 |
| 2019/0117997 A1* | 4/2019 | Fredriksson | G16H 20/40 |
| 2019/0240509 A1* | 8/2019 | Kuusela | A61N 5/103 |
| 2019/0388708 A1* | 12/2019 | Kumar | A61N 5/103 |
| 2021/0252307 A1* | 8/2021 | Kontaxis | A61N 5/1047 |

OTHER PUBLICATIONS

European Communication pursuant to Article 94(3) EPC for European Application No. 19158070.3, dated Feb. 1, 2022.

* cited by examiner

METHODS FOR INVERSE PLANNING

CROSS REFERENCE TO RELATED APPLICATIONS

This non-provisional application claims the benefit under 35 U.S.C. § 119(e) to U.S. Provisional Application No. 62/633,418, filed on Feb. 21, 2018, which is hereby expressly incorporated by reference into the present application.

FIELD OF THE INVENTION

The present invention relates to the field of radiotherapy. In particular, the invention relates to methods and systems for planning and optimizing treatment sessions of a patient in radiotherapy systems.

BACKGROUND OF THE INVENTION

The development of surgical techniques has made great progress over the years. For instance, patients in need of brain surgery may instead have non-invasive surgery which drastically reduces the trauma to the patients.

Systems for non-invasive surgery include the Leksell Gamma Knife® Icon™ and the Leksell Gamma Knife® Perfexion, which provide such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which, by itself, is insufficient to damage intervening tissue. However, tissue destruction occurs where the radiation beams from a plurality of radiation sources intersect or converge, causing the radiation to reach tissue-destructive levels. The point of convergence is hereinafter referred to as the "focus point".

Treatment plan optimization in radiotherapy, including for example gamma knife radiosurgery, aims at delivering sufficiently high dose to the target volume within the patient (e.g. in treatment of tumours) at the same time as the dose delivered to adjacent normal tissue is minimized. In treatment plan optimization, at least three competing factors have to be considered: delivering a sufficiently high dose to the target volume, sparing the surrounding normal or healthy tissue and keeping the treatment time as short as possible.

The treatment plan optimization is a process including optimizing the relative isocenter locations or beam directions, the beam shape settings (e.g. collimator configuration) and the fluences. In, for example, the Leksell Gamma Knife® Icon™ and the Leksell Gamma Knife® Perfexion the treatment plan optimization may include optimizing the number of shots being used, the collimator configuration of each shot, the shot times, and the position of the shot. The irregularity and size of a target volume greatly influence relative isocenter locations or beam directions, the beam shape settings (e.g. collimator configuration) and the fluences used to optimize the treatment.

In treatment planning, inverse treatment planning has gained more and more interest. Inverse planning generally refers to the stage in treatment planning where a deliverable treatment plan is sought, such that a number of criteria are satisfied. Inverse planning can be contrasted to forward planning, where the operator manually places, weights and shapes shots. The promises of inverse planning are shorter planning times and higher quality plans. Inverse planning is sometimes tightly integrated with forward planning, e.g. in the software accompanying the Leksell Gamma Knife: Leksell GammaPlan®. It is based on relative isodoses and uses metrics that are well-known in radiosurgery. This facilitates the transition from forward to inverse planning, and is presumably one of the reasons for the widespread adoption of inverse planning. A downside of relative isodose-based inverse planner and the complexity of the objectives is that the resulting optimization problem is inherently difficult to solve. In realistic cases it requires a compromise between computation time and the risk of ending up in a poor local optimum. This makes it difficult to explore what trade-offs are achievable—especially in complicated cases with multiple conflicting objectives. For example, a multi-metastases case where at least one metastasis is adjacent to an organ at risk. Incidentally, in such a case it might also be desirable to specify some criteria that must be met. In present inverse planners criteria for organs at risk (OAR) cannot be set.

Historically in inverse treatment planning for Gamma Knife radiosurgery, the relative isodoses are the fundamental object of interest. This is a heuristic motivated by the dose fall-off being the steepest for a certain isodose level, which should coincide with the target boundary. Incidentally, this is true for a single shot but need not be true when the dose distribution is the sum of contributions from multiple shots. Note that utilizing steep gradients presupposes high positional accuracy. For an isocenter the optimization variables are the position, collimator configuration and beam-on time. The isocenter locations are moved during the optimization and the collimator configuration is treated as a discrete element in the set of all possible collimator configurations. Organs at risk are not handled explicitly in the objective function, which can be a severe limitation. Evidently, tolerance doses for organs at risk are given in absolute dose but in the present mode of planning, absolute dose is assigned only after completing the plan. This results in an optimization problem that is very hard in the sense that any solution method requires either extensive computations or runs the risk of returning unsatisfactory solutions.

In improved inverse treatment planning methods provided by the applicant, a number of objectives reflecting clinical criteria for regions of interest, including one or more targets to be treated during treatment of the patient, one or more organs at risk and/or healthy tissue are set and radiation dose profiles to be delivered to the target or targets are generated. A convex optimization problem that steers the delivered radiation according to the objectives is provided and dose profiles for specific treatment configurations including beam shape settings for the radiation dose profiles are calculated using the convex optimization problem. Thereafter, a treatment plan, including determining the radiation dose profiles to be delivered during treatment based on the treatment configurations are created, wherein each radiation dose profile is modelled by a spatial dose volume distribution of radiation, the shape of the spatial distribution depending on the beam shape settings and an optimal treatment plan that satisfies the clinical criteria is selected.

However, there is still a need of more efficient methods for planning and optimizing the treatment.

SUMMARY OF THE INVENTION

An object of the present invention is to provide improved methods and systems for planning and optimizing treatment sessions of a patient in radiotherapy systems.

This and other objects are fulfilled by the present invention as defined by the independent claims. Preferred embodiments are defined by the dependent claims.

The term "target" or "target volume" refers to a representation of a target of a patient to be treated during radiotherapy. The target may be a tumour to be treated with radiotherapy. Typically, the representation of the target is obtained by, for example, non-invasive image capturing using X-ray or nuclear magnetic resonance.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined period of time during which a shot is delivered to the target volume.

The term "constraint" refers to constraints on the optimization variable, either directly, e.g. enforcing non-negative beam-on times, or indirectly, e.g. enforcing a minimum dose delivery to a certain volume. Also, constraint may refer to constraints that must not be violated (hard constraints) and/or constraints for which violations are allowed but penalized in the objective function (soft constraints).

The term "voxel" is used in the context of this application and refers to volume elements on a grid, which may be anisotropic in a three-dimensional space.

The term "frame description" includes at least an objective function and/or constraint for a set of voxels.

The present invention can, for example, be used in radiotherapy. Radiotherapy is used to treat cancers and other ailments in mammalian (e.g., human and animal) tissue. One such radiotherapy device is a Gamma Knife, which irradiates a patient with a large number of low-intensity gamma rays that converge with high intensity and high precision at a target (e.g., a tumour). Another radiotherapy device uses a linear accelerator, which irradiates a tumour with high-energy particles (e.g., photons, electrons, and the like). Still another radiotherapy device, a cyclotron, uses protons and/or ions. Another form of radiotherapy is brachytherapy, where a radiation source is placed inside or next to the area requiring treatment. The direction and shape of the radiation beam should be accurately controlled to ensure that the tumour receives the prescribed radiation dose, and the radiation from the beam should minimize damage to the surrounding healthy tissue, often called the organ(s) at risk (OARs). Treatment planning can be used to control radiation beam parameters, and a radiotherapy device effectuates a treatment by delivering a spatially varying dose distribution to the patient.

The present invention is for example used in connection with treatment planning of treatment provided by means of a radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

The present invention may also be used in connection with treatment planning in radiotherapy.

The present invention may further be used in brachytherapy. Brachytherapy is a form of radiotherapy where a sealed radiation source is placed inside or next to the area requiring treatment. Brachytherapy involves the precise placement of short-range radiation-sources (radioisotopes, Iodine-125 for instance) directly at the site of the cancerous tumour. Brachytherapy treatment planning often involves optimization methods to calculate the dwell times and dwell positions of the radioactive source along specified applicator paths. Inverse planning methods for brachytherapy aim at obtaining adequate target coverage and maximum sparing of critical structures. In geometric optimization, the relative dwell times are determined by the geometry of the implant by assigning an individual weighting factor for the dwell time at each dwell position that is inversely proportional to the dose contribution from neighboring source locations.

Hence, the optimization problem, which in preferred embodiments is a convex optimization problem, steers the delivered radiation according to the objectives and dose profiles for specific treatment configurations including source strengths and/or dwell times are calculated using the optimization problem. Thereafter, a treatment plan, including determining the radiation dose profiles to be delivered during treatment based on the treatment configurations can be created, wherein each radiation dose profile is modelled by a spatial dose volume distribution of radiation, the shape of the spatial distribution depending on the settings and an optimal treatment plan that satisfies the criteria can be selected.

According to embodiments of the present invention, there is provided a method for dose or treatment planning for a radiotherapy system comprising a radiotherapy unit. A spatial dose delivered can be changed by adjusting beam shape settings, wherein delivered radiation is determined using an optimization problem that steers the delivered radiation according to objectives reflecting criteria for regions of interest including at least one of: targets to be treated during treatment of the patient, organs at risk and/or healthy tissue. The method comprises the steps of determining an inner set of voxels that encompasses the outer surface of a target volume, providing a first frame description, which include at least a first objective function and/or constraint for the inner set of voxels, where the first objective function includes at least one objective reflecting criteria for the inner set of voxels.

Then, at least one outer set of voxels encompassing the target volume and the inner set of voxels is determined and a frame description, including an objective function (or functions) and/or constraint for the outer set of voxels, is provided where each reflecting criteria for the outer set of voxels. The frame descriptions are then used in the optimization problem that steers the delivered radiation.

The optimization problem, which in preferred embodiments is a convex optimization problem, steers the delivered radiation according to the objectives and dose profiles for specific treatment configurations including beam shape settings for the radiation dose profiles are calculated using the optimization problem. Thereafter, a treatment plan, including determining the radiation dose profiles to be delivered during treatment based on the treatment configurations can be created, wherein each radiation dose profile is modelled by a spatial dose volume distribution of radiation, the shape of the spatial distribution depending on the beam shape settings and an optimal treatment plan that satisfies the criteria can be selected.

According to a further aspect, there is provided a method for treatment planning for a radiotherapy, wherein delivered radiation is determined using an optimization problem that steers the delivered radiation according to objectives reflecting criteria for regions of interest, that include at least one of: at least one target to be treated during treatment of the patient, organs at risk and/or healthy tissue. The method comprising the steps of: determining an inner set of voxels that encompasses the outer surface of a target volume; providing a first frame description for an inner set of voxels, the first frame description reflecting criteria of the inner set of voxels; determining at least one outer set of voxels encompassing the target volume and the inner set of voxels; providing a respective frame description for each outer set of voxels, each frame description reflecting criteria for the outer set of voxels; and using the frame descriptions in the optimization problem that steers the delivered radiation.

According to another aspect of the present invention, there is provided a method for treatment planning for a radiotherapy system comprising a radiotherapy unit having a fixed radiation focus point. A spatial dose distribution surrounding the focus point can be changed by adjusting beam shape setting, including collimator settings, where the collimator is arranged in sectors and has a plurality of collimator passage inlets directing radiation emanating from radioactive sources of a source carrier arrangement of the therapy system to the focus point. The method comprises the steps of determining an inner set of voxels that encompasses the outer surface of a target volume, providing a first frame description for the inner set of voxels, where the first frame description reflects criteria for the inner set of voxels. Then, at least one outer set of voxels encompassing the target volume and the inner set of voxels is determined and a frame description for the outer set of voxels is provided where each reflecting criteria for the outer set of voxels. The frame descriptions are then used in the optimization problem that steers the delivered radiation.

The optimization problem, which in preferred embodiments is a convex optimization problem, steers the delivered radiation according to the objectives and dose rates are calculated for specific treatment configurations including sector and collimator settings and irradiation time for isocenters using the optimization problem. Then, treatment plans can be created including determining shots to be delivered during treatment based on the treatment configurations, wherein each shot is modelled by a spatial dose volume distribution of radiation represented by a three-dimensional voxel representation, wherein the shape of the spatial distribution depending on the specific sector and collimator setting and irradiation time. Finally, an optimal treatment plan that satisfies the criteria can be selected.

According to embodiments of the present invention, the inner and outer set of voxels are shaped as shells. For example, a distance between an inner surface of each shell and an outer surface of the target may be the same in all directions or depend on direction, for example, it may be different in x- y- and z-directions.

In embodiments of the present invention, the objectives for the inner and/or outer set of voxels include delivered dose to the set of voxels.

According to embodiments of the present invention, the method further comprises setting a weight corresponding to an importance of the objective or objectives of the objective functions for the inner and/or outer set of voxels, respectively, and/or for each individual voxel in the inner and/or outer set of voxels, and/or for subset of voxels in the inner and/or outer set of voxels.

In embodiments of the present invention, the method further comprises setting a scalar weight corresponding to an importance of the objective or objectives of an objective function for a target volume.

According to embodiments of the present invention, each weight governs an importance of different objectives.

In embodiments of the present invention, the inner and outer set of voxels may have a uniform thickness measured in number of voxels or in distance, for example, in mm between inner and outer boundary or surface. Furthermore, the inner and outer set of voxels may have a non-uniform thickness measured in voxels or in distance, for example, in mm between inner and outer boundary or surface.

According to embodiments of the present invention, a weight for the inner set of voxels is selected to promote selectivity, and wherein a weight of an outer set of voxels is selected to promote high gradient outside the target/targets.

In embodiments of the present invention, an inner surface of a first outer set of voxels encompasses an outer surface of the inner set of voxels.

According to embodiments of the present invention, at least one frame description comprise an approximation of an integral, over the voxels in the set of voxels, of a function for dose delivery that depends on the distance to an outer surface of the target volume.

In embodiments of the present invention, the method further comprises calculating dose profiles for specific treatment configurations including beam shape settings for the radiation dose profiles using the optimization problem, creating treatment plans including determining the radiation dose profiles to be delivered during treatment based on the treatment configurations, wherein each radiation dose profile is modelled by a spatial dose volume distribution of radiation, the shape of the spatial distribution depending on the beam shape settings, and selecting an optimal treatment plan that satisfies the criteria.

According to embodiments of the present invention, the method further comprises calculating dose rates for specific treatment configurations including sector and collimator settings and irradiation time for the isocenters using the optimization problem, creating treatment plans including determining shots to be delivered during treatment based on the treatment configurations, wherein each shot is modelled by a spatial dose volume distribution of radiation, the shape of the spatial distribution depending on the specific sector and collimator setting and irradiation time, and selecting an optimal treatment plan that satisfies the criteria.

In embodiments of the present invention, the method further comprises defining a set of beam directions, modelling radiation dose profiles to be delivered to the target as a plurality of beamlets each having a beamlet intensity, setting a number of objectives reflecting criteria for the target, providing an optimization problem that steers the delivered radiation according to the objectives so as to create fluence maps, wherein the fluence maps define the beamlet intensities for each of the beamlets, creating treatment plans based on fluence maps and criteria for the target, and selecting an optimal treatment plan that satisfies the criteria.

According to embodiments of the present invention, the method comprises positioning of radiation source(s) relative to the patient, including generating fixed isocenter positions.

In embodiments of the present invention, the radiation source positions are generated as a set of continuous points in the target volume based on basis functions, wherein the points are fixed during the treatment planning.

According to embodiments of the present invention, the objectives include delivered dose to target, delivered dose to a boundary space surrounding the target, delivered dose to regions classified as a risk organ, and/or beam-on time penalization.

According to embodiments of the present invention, dose rates for specific treatment configurations including sector and collimator settings and irradiation time are calculated using the convex optimization problem for predetermined isocenters within the volume.

An optimized dose plan determined by means of the present invention, may be transferred to a radiotherapy system for use in the treatment of the patient. The dose plan determined by the invention may also or alternatively be used as input in a treatment optimization procedure where the number of shots, position of the shots and the shot sizes defined during the volume filling according to the invention serves as basis in an optimization of the number of shots, the position and the beam-on time of the respective shots and the shots sizes.

According to still another aspect of the present invention, there is provided a treatment planning computer structure in which the method according to the present invention may be implemented.

In embodiments of the present invention, the treatment plan computer structure may utilize methods according to the present invention and may be integrated into a system for delivering intensity modulated radiation treatment (IMRT) including a radiation source that generates at least one radiation beam. A beam shaping device, e.g. a multi-leaf collimator or a conical collimator, may be disposed between the radiation source and the patient. The collimator is communicatively connected to the treatment planning computer structure and is configured to modify the plurality of beamlets to deliver according to optimal treatment plan, i.e. a fluence map based on the beam shape settings determined, to the patient.

In further embodiments of the present invention, the treatment plan computer structure may utilize methods according to the present invention that may be integrated into a radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The collimator body is communicatively connected to the treatment planning computer structure to deliver according to optimal treatment plan to the patient.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1A:
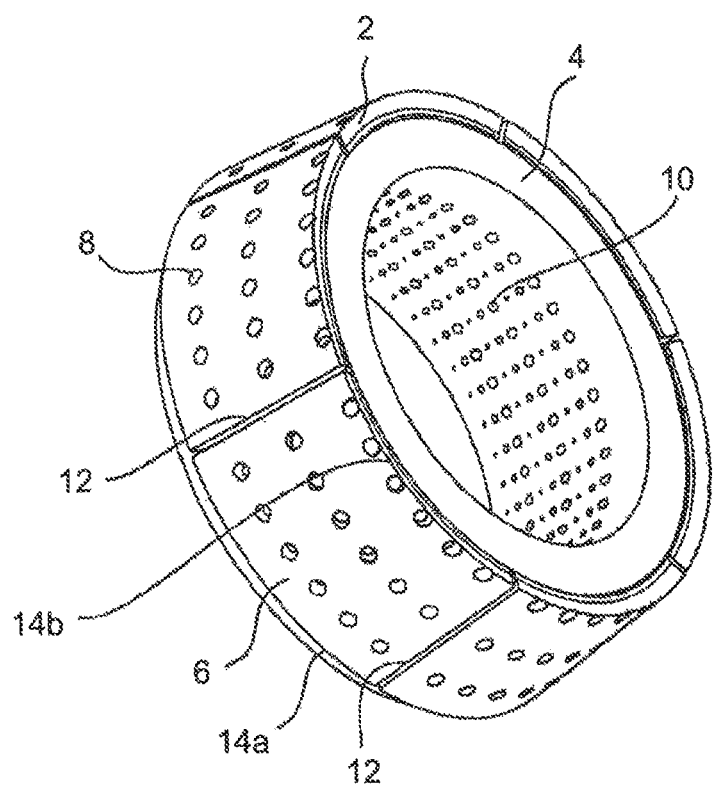
FIG. 1a is a perspective view of an assembly comprising a source carrier arrangement surrounding a collimator body in which the present invention may be used.
Figure 1B:
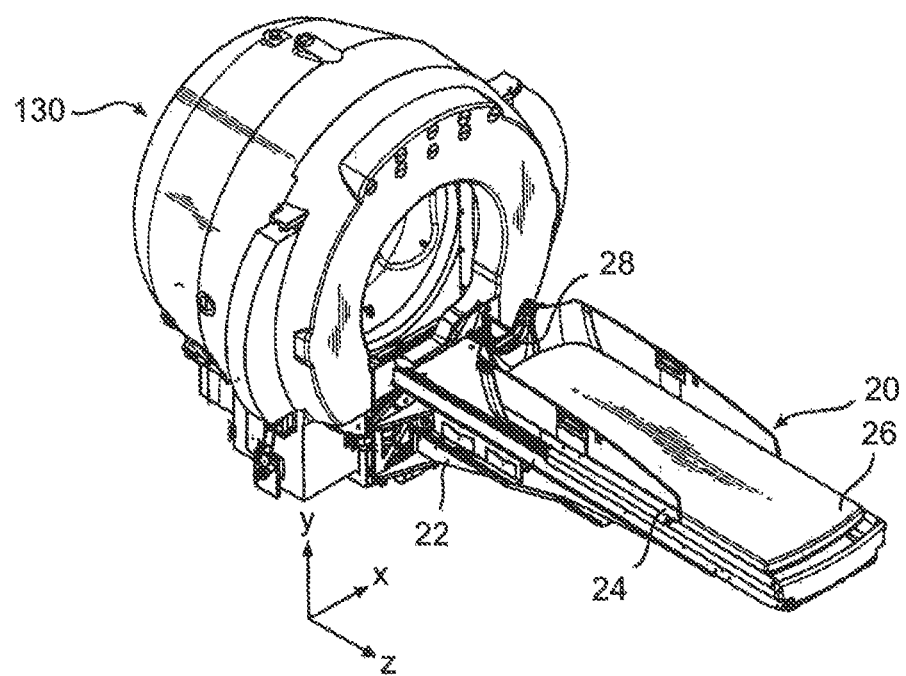
FIG. 1b shows a radiotherapy device in which the assembly of FIG. 1 may be used.

With reference first to FIGS. 1a and 1b, an exemplary radiotherapy device in which a treatment plan developed using the present invention can be used for treatment of a patient.

FIG. 1a is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1a there is a larger number of internal mouths 10 or holes of the collimator passages than the number of apertures 8 for receiving radioactive sources. In this particular case, there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus point. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

In FIG. 1*b*, aradiotherapy system including a radiotherapy device 130 having a source carrier arrangement as shown in FIG. 1*b*, and a patient positioning unit 20 is shown. In the radiotherapy unit 130, there are thus provided radioactive sources, radioactive source holders, a collimator body, and external shielding elements. The collimator body comprises a large number of collimator channels directed towards a common focus point, as shown in FIG. 1*b*.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit. The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Figure 2A:
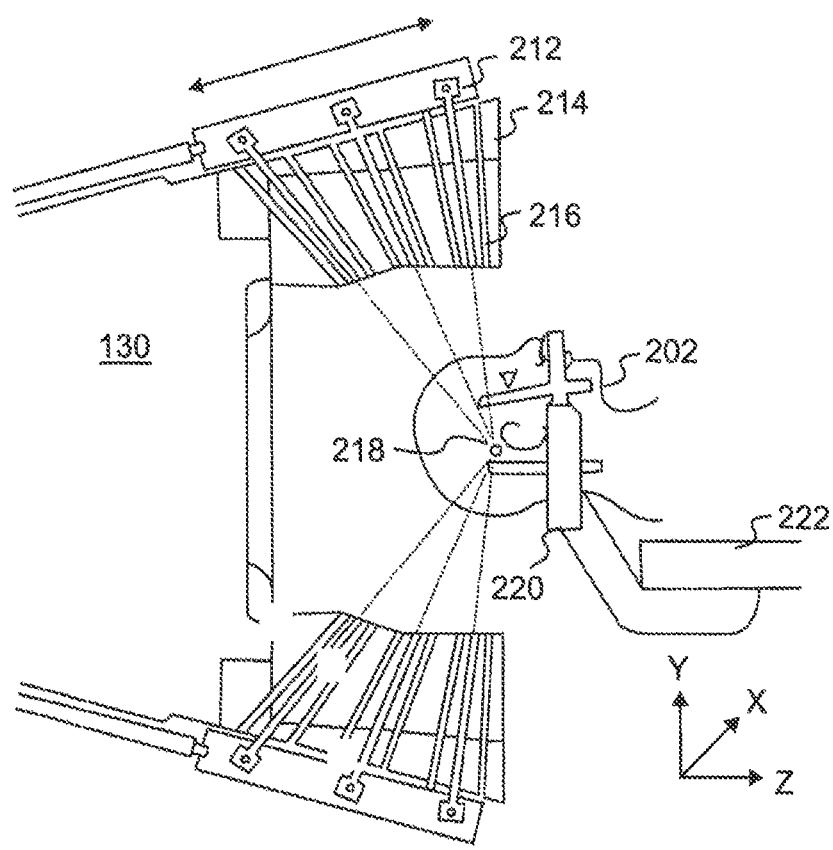
FIG. 2a shows a radiotherapy device, a Gamma Knife, in which the present invention may be used.

FIG. 2*a* illustrates a radiotherapy device 130, a Gamma Knife in which the present invention can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiosurgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumour.

Figure 2B:
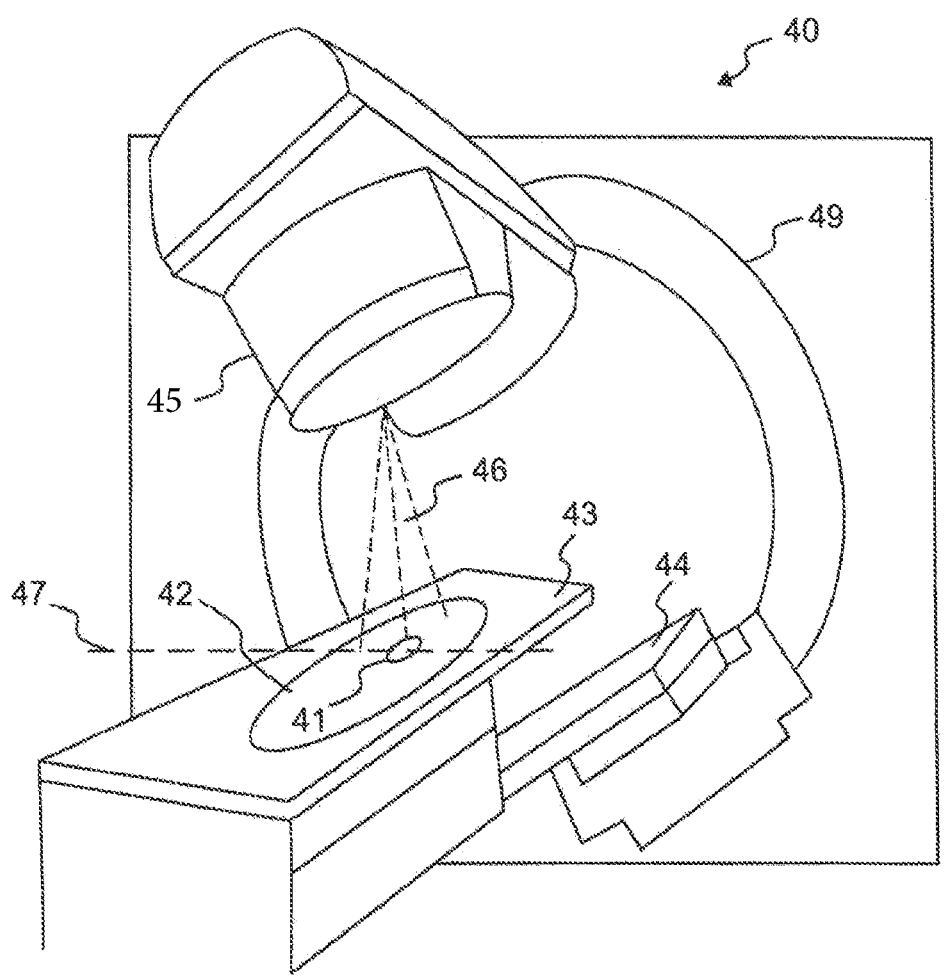
FIG. 2b shows another radiotherapy device, a linear accelerator, in which the present invention can be used.

FIG. 2*b* illustrates another radiotherapy device 40, a linear accelerator 10 in which the present invention can be used. Using a linear accelerator 40, a patient 42 may be positioned on a patient table 43 to receive the radiation dose determined by the treatment plan. Linear accelerator 40 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45 is usually referred to as the "isocenter". The patient table 43 may be motorized so that the patient 42 can be positioned with the tumour site at or close to the isocenter 41. The radiation head 45 may rotate about a gantry 47, to provide patient 42 with a plurality of varying dosages of radiation according to the treatment plan.

In the following, the present invention will be described in more detail with reference to embodiments. As been discussed above, the inverse planning according to the invention is formulated as optimization problem or problems, which preferably is convex and thereby the solutions is reproducible and can be found quick and efficiently. The clinical criteria that provides basis for the evaluation are inherently non-convex and are therefore translated into convex "surrogates". In the present invention, two or more geometric structures are introduced for each target volume and the target volume is hence encompassed by two set of voxels or shells.

Figure 4:
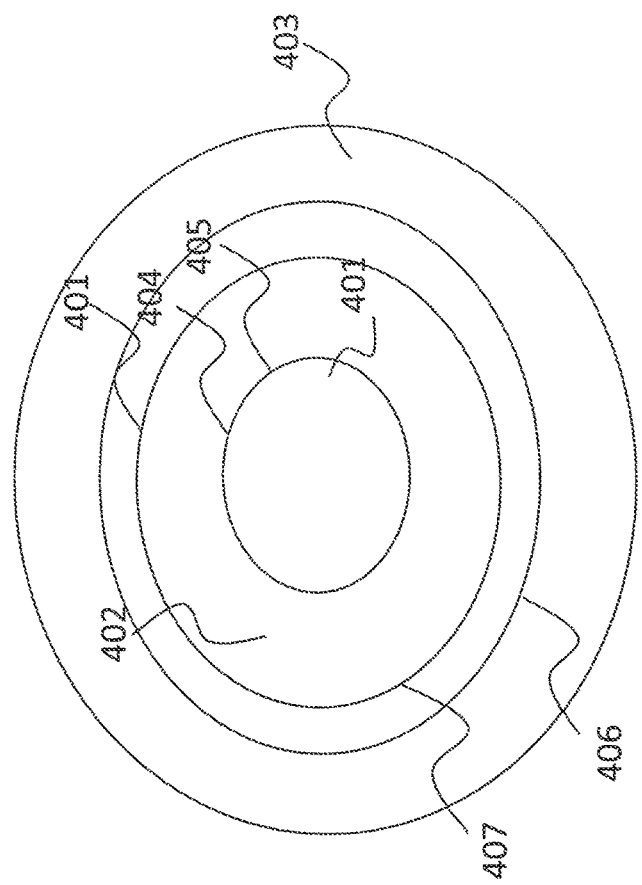
FIG. 4 shows the geometry of an inverse planning problem in a simplified two-dimensional illustration according to another embodiment of the present invention.
Figure 3:
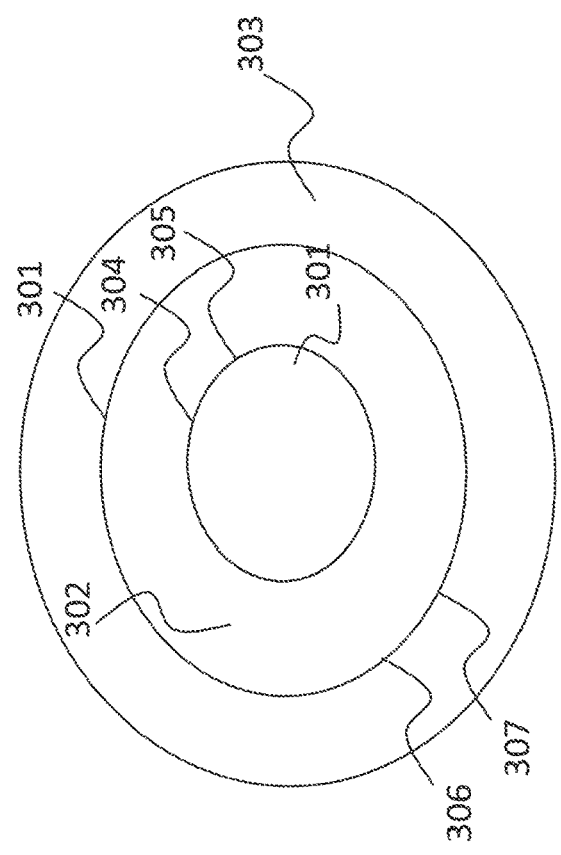
FIG. 3 shows the geometry of an inverse planning problem in a simplified two-dimensional illustration according to an embodiment of the present invention.

In FIG. 3, the geometry of an inverse planning problem in a simplified two-dimensional illustration is shown. The structures are shown as rings but since the target volume is three-dimensional, the rings are consequently sets of voxels, or in other words shells or sphere layers shapes, and encompasses the target volume (or tumour value). The target volume 301 is thus encompassed by the inner shell 302 and, at least one, outer shell 303. The inner shell 302 promotes selectivity and the outer shell 303 promotes gradient index, respectively. The inner shell 302 encompasses the target volume 301 and its inner surface 305 may be directly adjacent to the outer surface 304 of the target volume 301, as shown in FIG. 3 while the inner surface 306 of the outer shell 303 in the example in the FIG. 3 may be adjacent to outer surface 307 of the inner shell 302. However, the outer shell 303 or outer shells may be located with a radial distance from the outer surface 305 of the inner shell 302, as shown in FIG. 4. The radial distance may be different in different directions, for example, the distance may be different in x- y- and z-directions.

Hence, the target volume 401 is encompassed by the inner shell 402 and, at least one, outer shell 403. The inner shell 402 promotes selectivity and the outer shell 403 promotes gradient index, respectively. The inner shell 402 encompasses the target volume 401 and its inner surface 405 may be directly adjacent to the outer surface 404. In this embodiment, the inner surface 406 of the outer shell 403 is located at a distance from the outer surface 407 of the inner shell 402.

In FIGS. 3 and 4, the shells are illustrated having regularly shaped inner surfaces, but it is understood that it is only schematic illustration, for example, the inner surfaces and outer surfaces may be irregular for example, due to different distances between inner surface of a shell and outer surface of the target in different directions.

Further, the shells are illustrated as having a uniform thickness measured in number of voxels or in distance, for example, in mm between inner and outer boundary or surface but the inner and outer set of voxels may instead have a non-uniform thickness measured in voxels or in distance, for example, in mm between inner and outer boundary or surface.

The frame description for each shell is formulated so that each voxel can be individually considered. According to an embodiment, the frame description is an approximation of an integral, namely a sum where the terms correspond to the voxels at distance $r_j$ from the outer surface 304 of the target volume 301 and may be given by:

$$\frac{1}{M}\sum_{j=1}^{M}\frac{1}{D(r)N_j}\sum_{i=1}^{N_j} w_{ij}\max((\varphi_j x)_i - D(r), 0),$$

where x is the irradiation times for each isocenter, sector, and collimator setting, $\varphi_j$ is the dose rate matrix for voxels at distance $r_j$, D(r) is a function describing the desired dose as a function of the distance from the target surface, $N_j$ is the number of voxels at distance $r_j$, r is the vector of all target distances and $w_{ij}$ is a scalar weight, which in embodiments can be varied voxel-by-voxel. In embodiments of the present invention, the term D(r) is used, describing that the desired dose varies in different directions.

According to embodiments, two shells are applied having a size or volume that depend on the volume of the target. Penalizing dose in these two shells will correspond to promoting the two non-convex quantities selectivity and gradient index, respectively. The size or volume of the outer shell is preferably chosen so that a desired gradient index can be achieved.

The objective function may be formulated voxel-by-voxel for the target and the two encompassing shells. According to embodiments of the present invention, a minimal objective function for one target and thus two shells, which easily can be generalized to more than one target, with neither OAR nor beam-on time penalization, can be formulated as follows:

$$\operatorname*{argmin}_{x} f =$$

$$\frac{w_1}{D_T N_T} \sum_{i=1}^{N_T} \max(D_T - (\varphi_T x)_i, 0) + \frac{w_2}{D_T N_{IR}} \sum_{i=1}^{N_{IR}} \max((\varphi_{IR} x)_i - D_T, 0) +$$

$$\frac{w_3}{(D_T/2) N_R} \sum_{i=1}^{N_R} \max\left((\varphi_R x)_i - \frac{D_T}{2}, 0\right)$$

$$x \geq 0,$$

where x is the irradiation times for each isocenter, sector and collimator setting, $w_1$, $w_2$, $w_3$ are the weights for the target, inner and outer ring respectively. $D_T$ is the prescription dose, $N_i$ is the number of target voxels in the structure i∈{T, IR, OR} and $\varphi_i$ is the dose rate in the respective structure. The first term penalizes underdosing of the target, the second term penalizes overdosing of the inner shell and the third term penalizes dose in the outer shell that exceeds $D_T/2$, where the gradient index is defined as the volume with dose exceeding $D_T/2$ over volume of the dose exceeding $D_T$. The three terms are good convex surrogates for coverage, selectivity and gradient index, respectively. The objective function is a weighted sum where the three weights $w_1$, $w_2$, $w_3$ governs the relative importance of the different objectives, and thus, the importance of coverage, selectivity and gradient index respectively. With one weight, or at least one weight, corresponding to each clinical metric, the translation of the clinical objectives to the desired plan qualities can be obtained by adjusting weights of the objective function before the optimization is performed. Since the problem is convex, the complete set of weights will span a Pareto surface. Thus, the extension of the current problem to one of multicriteria optimization is straightforward.

Figure 5:
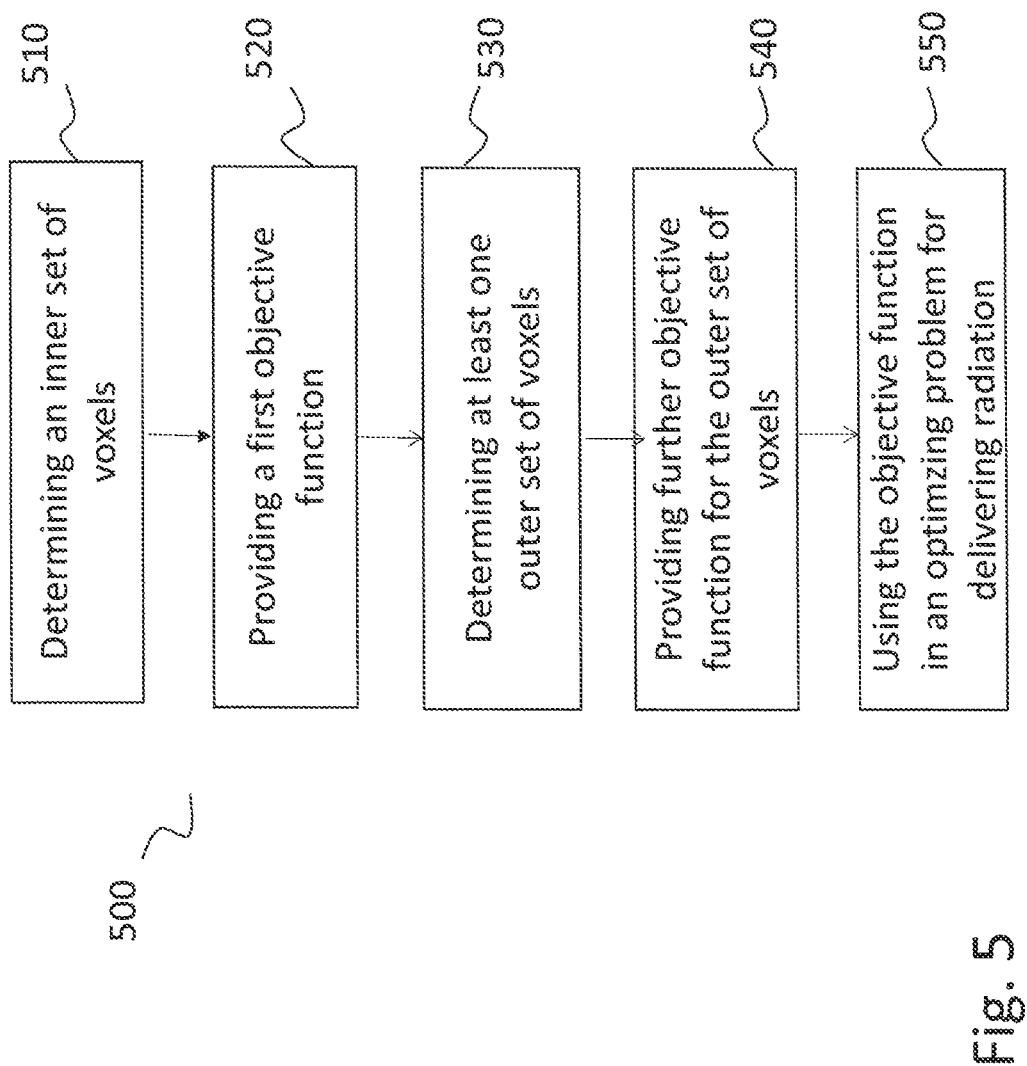
FIG. 5 is a flow diagram illustrating an embodiment of the present invention.

Turning now to FIG. 5, a general method according to the present invention will be described. The method may be used for treatment planning for a linear accelerator, for example, in intensity modulated radiotherapy as well as in Volumetric Modulated Arc Therapy utilizing multi-leaf collimators. In a linear accelerator, electron beams are generated by an electron accelerator including an electron gun, a wave guide and a guide magnet. The electron beam impinges on a target made of high atomic number materials thereby creating ionizing radiation. Ionizing radiation can be modeled as a plurality of beamlets each having a beamlet intensity that can be modelled according to a fluence map. The fluence map is determined in the optimization. Moreover, the method may also be used in treatment planning for radiotherapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

First in the method 500, at step 510, an inner set of voxels that encompasses the outer surface of a target volume is determined.

Then, in step 520, a first frame description for an inner set of voxels is provided, where the first frame description reflecting criteria for the inner set of voxels.

Thereafter, at step 530, at least one outer set of voxels encompassing the target volume and the inner set of voxels is determined.

At step 540, frame description(s) for at least one outer set of voxels is provided, each reflecting criteria for that outer set of voxels.

The frame descriptions are then used in the optimization problem that steers the delivered radiation at step 550.

Figure 6:
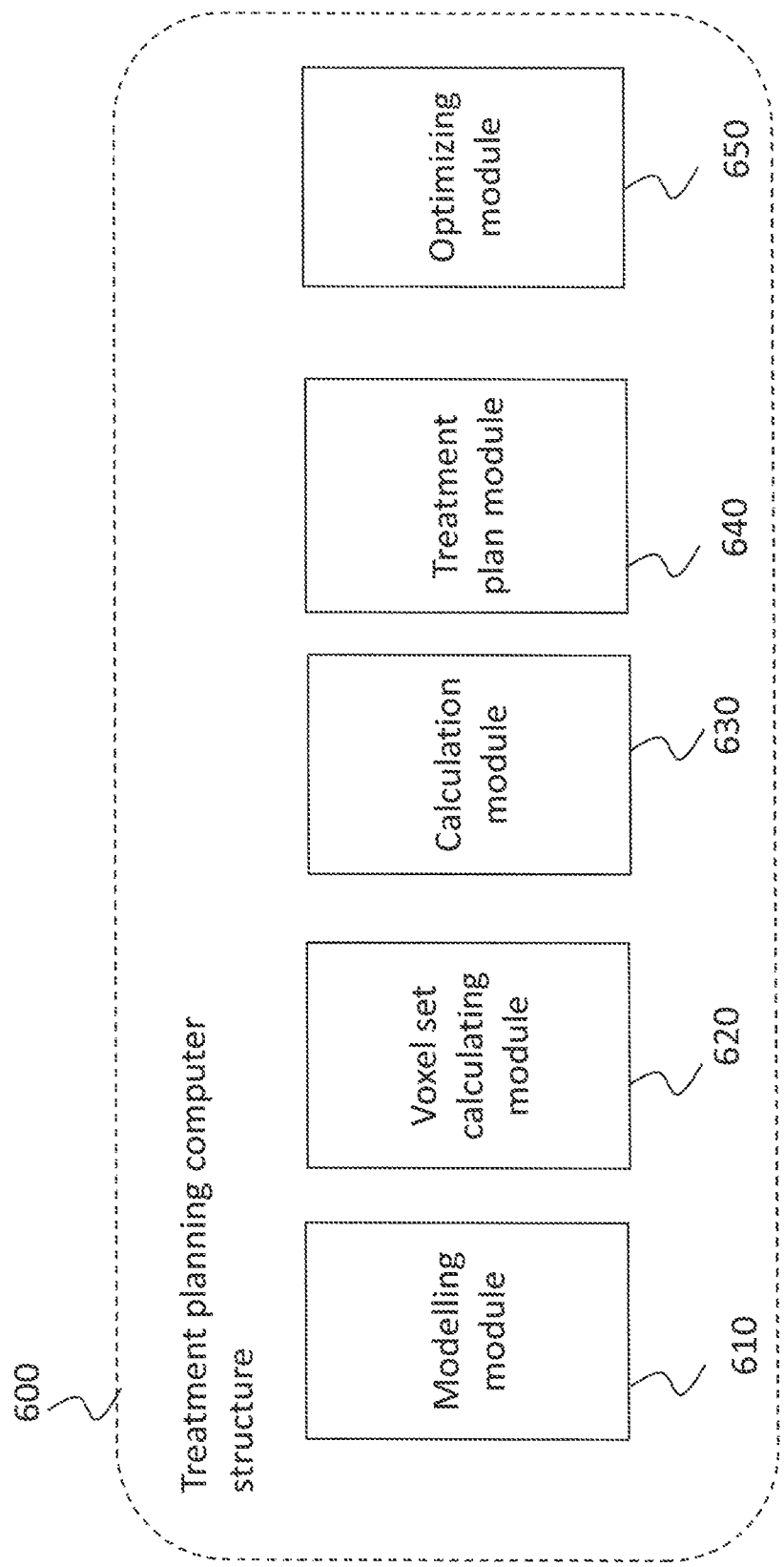
FIG. 6 shows an embodiment of a treatment planning computer structure according to the present invention.

Turning now to FIG. 6, a treatment planning computer structure in which the method according to the present invention may be implemented will be described. The treatment planning computer structure 600 may include a modelling module 610 configured for modelling a volume of a patient as a three-dimensional voxel representation or for obtaining such a three-dimensional voxel representation, wherein the volume includes a target volume to be treated during a treatment of the patient in a radiotherapy unit. A voxel set calculating module 620 calculates or determines an inner set of voxels that encompasses o the outer surface of a target volume based on a first frame description (e.g. including an objective function and/or one or more constraints for an inner set of voxels) for an inner set of voxels, where the first frame description reflecting criteria for the inner set of voxels, and at least one outer set of voxels encompassing the target volume and the inner set of voxels based on frame description(-s), e.g. including an objective function (or functions) and/or one or more constraints for outer set of voxels, where each reflecting criteria for the outer set of voxels. In one example, the objective functions may be formulated voxel-by-voxel for the target and the two encompassing shells or inner and outer set of voxels, as also shown above:

$$\operatorname*{argmin}_{x} f =$$

$$\frac{w_1}{D_T N_T} \sum_{i=1}^{N_T} \max(D_T - (\varphi_T x)_i, 0) + \frac{w_2}{D_T N_{IR}} \sum_{i=1}^{N_{IR}} \max((\varphi_{IR} x)_i - D_T, 0) +$$

$$\frac{w_3}{(D_T/2) N_R} \sum_{i=1}^{N_R} \max\left((\varphi_R x)_i - \frac{D_T}{2}, 0\right)$$

$$x \geq 0,$$

where x is the irradiation times for each isocenter, sector and collimator setting, $w_1$, $w_2$, $w_3$ are the weights for the target, inner and outer ring respectively. $D_T$ is the prescription dose, $N_i$ is the number of target voxels in the structure i∈{T, IR, OR} and $\varphi_i$ is the dose rate in the respective structure.

Further, a calculation module 630 configured for generating radiation dose profiles to be delivered to the target, for providing the convex optimization problem including, for example, the objective functions for the inner and outer set of voxels shown above, that steers the delivered radiation according to the objectives, and for calculating dose profiles for specific treatment configurations including beam shape settings for the radiation dose profiles are calculated using the convex optimization problem. A treatment plan module 640 is configured for creating treatment plans including determining the radiation dose profiles to be delivered during treatment based on the treatment configurations, wherein each radiation dose profile is modelled by a spatial dose volume distribution of radiation represented by a three-dimensional voxel representation, the shape of the spatial distribution depending on the beam shape settings. An optimizing module 650 is configured for selecting an optimal treatment plan that satisfies the clinical criteria. In embodiments of the present invention, the optimization, i.e. selecting an optimal treatment plan that satisfies the clinical criteria, is performed and then the treatment plan including determining the radiation dose profiles to be delivered during treatment based on the treatment configurations is created.

In embodiments of the present invention, the treatment plan computer structure 600 may utilize a method as described in FIG. 3 or 5 and may be integrated into a system for delivering intensity modulated radiation treatment including a radiation source that generates at least one radiation beam and a structure for generating a plurality of beamlets.

Figure 7:
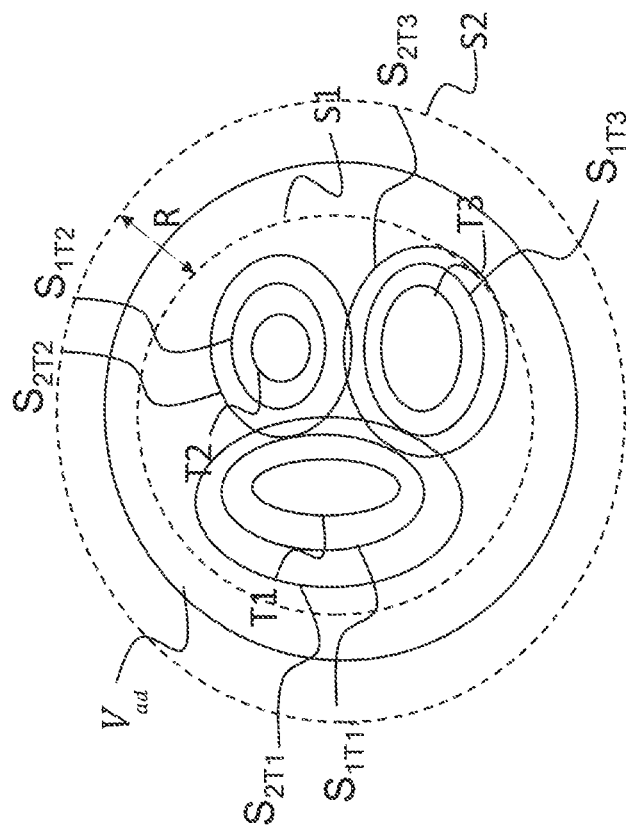
FIG. 7 shows the geometry of an inverse planning problem in a simplified two-dimensional illustration according to a further embodiment of the present invention.

The methods described herein according to the present invention may furthermore be used in combination with a method for providing a low overall dose volume. In FIG. 7, this is described in more detail. It should however be noted that FIG. 7 shows the geometry of in a simplified two-dimensional illustration. The structures are shown as rings but since the target volumes is three-dimensional, the rings are consequently shells or sphere layers shapes and encompasses the target volume (or tumour value).

There is an abundance of clinical data showing that adverse cognitive effects may occur if large volumes, $V_{ad}$, of normal tissue is irradiated by relatively low dose. In particular, this is the case when multiple targets are close to each other. In FIG. 7, three targets T1, T2, T3 are shown being close to each other. Further, inner and outer set of voxels, called rings below since the targets are three-dimensional they are shells in reality, are denoted by $S_{1T1}$, $S_{2T1}$, $S_{1T2}$, $S_{2T2}$, $S_{1T3}$, $S_{2T3}$.

The main problem is that the set of voxels, with volume equal to $V_{ad}$, depends on the dose distribution and will change during the optimization, leading to a non-convex optimization problem which is in general difficult to solve. To achieve a convex formulation it is therefore necessary to have a fixed geometry in which dose is penalized.

According to the present invention, a volume filling procedure or fill algorithm is applied, for example, a fill algorithm used in the Leksell Gamma Plan. One example of a suitable fill algorithm is described in a co-pending, not yet published, patent application by the same applicant.

Based on the use of the fill algorithm, a fixed low dose ring, R as shown in FIG. 7, of voxels can be created in the volume surrounding at least one target (T1, T2, T3). The voxels of this fixed volume can then be penalized giving an efficient low dose penalization. If there is assumed that there is a pair $(V_{ad}, D_{ad})$ where $D_{ad}$ is the dose at which adverse effects are significant if the volume is at least $V_{ad}$, see FIG. 4. For instance, there is clinical evidence suggesting an increased risk of radionecrosis if the volume receiving more than 10 Gy exceeds 13 cc, but the user could specify other values. According to the present invention, such adverse effects can be significantly reduced or eliminated by introducing a penalty term in the optimization problem. As mentioned above, a fill algorithm is used first, which is a pre-step to the optimization. In addition to providing the isocenter locations, the fill algorithm also gives the shot collimator configuration for each isocenter. By setting the prescription dose forcing the weights to be 1 for all shots, a realistic dose distribution can be calculated. To suppress doses to large volume a low dose ring is created and the algorithm for creating the low dose ring consists of the following steps. A fill algorithm is thus used to find isocenter locations and to determine shot collimator configurations for all isocenter locations. Prescription doses for the target(s), T1, T2, T3, are set. This gives irradiation times for all shots. Then, the dose distribution is calculated from the above configuration. Thereafter, the voxels, $SV_{ad}$, in the the 3D isodose volume of the dose distribution having a volume equal to $V_{ad}$ (after having added the target volumes) are identified. Then, a ring of voxels, R, is defined as the set difference between a contraction and an expansion of $SV_{ad}$, see FIG. 4, using, for example, a distance model:

$$\delta_r = \frac{1}{3\alpha}\left(\frac{\delta D}{D_{Fad}}\right) V_{ad}^{\frac{1}{3}},$$

$$\alpha \approx 0.65$$

$$\delta D_{contract} = 1 \ Gy$$

$$\delta D_{expand} = 1 \ Gy$$

Here $D_{F,ad}$ is the isodose in Gy corresponding to $V_{ad}$. A "ring size" corresponding to 1 Gy is a reasonable choice to include various dose distributions without introducing too many voxels in the optimization. Then, a penalization term is added in the objective function penalizing voxels with dose exceeding a threshold dose. In embodiments of the present invention, it may be in the following form:

$$\frac{w_{lr}}{N_r * D_{ad}} \sum_{i=1}^{N_{lr}} \max((\phi x)_i - D_{ad}, 0)$$

where the sum runs over voxels in the low dose ring and $w_{lr}$ is the optimization weight. This ring is treated in the same way as the outer ring(s) in the optimization.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. A method for treatment planning for a radiotherapy, wherein delivered radiation is determined using an optimization problem that steers the delivered radiation according to objectives reflecting criteria for regions of interest, that include at least one of: at least one target to be treated during treatment of a patient, organs at risk and/or healthy tissue; said method comprising the steps of:
controlling a voxel set calculating module for determining an inner set of voxels that encompasses an outer surface of a target volume, wherein the inner set of voxels is determined to be outside an outer surface of the target volume, and wherein an inner surface of the inner set of voxels is adjacent to the outer surface of the target volume;
controlling the voxel set calculating module for providing a first frame description for an inner set of voxels, said first frame description reflecting at least one criterion for the inner set of voxels;
controlling the voxel set calculating module for determining at least one outer set of voxels encompassing said target volume and said inner set of voxels, said at least one outer set of voxels being located outside said outer surface of the target volume and said inner set of voxels;
controlling the voxel set calculating module for providing a respective frame description for each outer set of voxels, each frame description reflecting at least one criterion for that outer set of voxels; and
controlling a calculation module to generate radiation dose profiles to be delivered to the target using said frame descriptions in the optimization problem that steers the delivered radiation.

2. The method according to claim 1, wherein the method is for treatment planning for a radiotherapy system, the radiotherapy system comprising a radiotherapy unit having a fixed radiation focus point, the method further comprising:
adjusting a beam shape setting, including collimator settings, to change a spatial dose distribution surrounding the focus point, said collimator being arranged in sectors and having a plurality of collimator passage inlets directing radiation emanating from radioactive sources of a source carrier arrangement of the therapy system to said focus point.

3. The method according to claim 1, wherein said inner and outer sets of voxels are shaped as shells, wherein a distance between an inner surface of each shell and an outer surface of the target is the same in all directions or depends on direction.

4. The method according to claim 1, wherein said objectives for said inner and/or outer set of voxels include delivered dose to said set of voxels.

5. The method according to claim 1, further comprising setting a weight corresponding to an importance of the objective or objectives of an objective functions for said inner and/or outer set of voxels, respectively, and/or for each individual voxel in said inner and/or outer set of voxels, and/or for subset of voxels in said inner and/or outer set of voxels.

6. The method according to claim 1, further comprising setting a scalar weight corresponding to an importance of the objective or objectives of an objective function for a target volume.

7. The method according to claim 1, wherein a weight for the inner set of voxels is selected to promote selectivity, and wherein a weight of an outer set of voxels is selected to promote high gradient outside the target/targets.

8. The method according to claim 1, wherein an inner surface of a first outer set of voxels encompasses an outer surface of the inner set of voxels.

9. The method according to claim 1, wherein the objective functions comprise an approximation of an integral, over the voxels in said set of voxels, of a function for dose delivery that depends on the distance to an outer surface of the target volume.

10. The method according to claim 1, further comprising:
controlling the calculation module for calculating dose profiles for specific treatment configurations including beam shape settings for the radiation dose profiles using said optimization problem;
controlling a treatment plan module for creating treatment plans including determining the radiation dose profiles to be delivered during treatment based on the treatment configurations, wherein each radiation dose profile is modelled by a spatial dose volume distribution of radiation, a shape of said spatial distribution depending on the beam shape settings; and
controlling an optimizing module for selecting an optimal treatment plan that satisfies the criteria.

11. The method according to claim 1, further comprising:
controlling the calculation module for calculating dose rates for specific treatment configurations including sector and collimator settings and irradiation time for isocenters using said optimization problem;
controlling a treatment plan module for creating treatment plans including determining shots to be delivered during treatment based on the treatment configurations, wherein each shot is modelled by a spatial dose volume distribution of radiation, a shape of said spatial distribution depending on the specific sector, collimator setting, and irradiation time; and
controlling an optimizing module for selecting an optimal treatment plan that satisfies the criteria.

12. The method according to claim 1, further comprising a step of positioning of radiation source(s) relative to said patient, wherein the step of positioning radiation source(s) includes generating fixed isocenter positions.

13. The method according to claim 1, further comprising a step of positioning of radiation source(s) relative to said patient, wherein the radiation source positions are generated as a set of continuous points in said target volume based on basis functions, wherein the set of continuous points are fixed during the treatment planning.

14. The method according to claim 1, wherein said objectives include delivered dose to target, delivered dose to a boundary space surrounding said target, delivered dose to regions classified as a risk organ, and/or beam-on time penalization.

15. The method according to claim 5, wherein each weight governs an importance of different objectives.

16. The method according to claim 10, further comprising:

controlling said calculation module for defining a set of beam directions;

controlling said calculation module for modelling radiation dose profiles to be delivered to said target as a plurality of beamlets each having a beamlet intensity;

controlling said calculation module for setting a number of objectives reflecting criteria for the target;

controlling said calculation module for providing an optimization problem that steers the delivered radiation according to the objectives so as to create fluence maps, wherein the fluence maps define the beamlet intensities for each of said beamlets;

controlling said treatment plan module for creating treatment plans based on fluence maps and criteria for the target; and controlling said optimizing module for selecting an optimal treatment plan that satisfies the criteria.

17. A method for treatment planning for a radiotherapy system, the radiotherapy system comprising a radiotherapy unit, wherein a spatial dose delivered can be changed by adjusting beam shape settings, wherein delivered radiation is determined using an optimization problem that steers the delivered radiation according to objectives reflecting criteria for regions of interest, that include at least one of: at least one target to be treated during treatment of a patient, organs at risk and/or healthy tissue; said method comprising the steps of:

controlling a voxel set calculating module for determining an inner set of voxels that encompasses an outer surface of a target volume, said inner set of voxels being located outside said outer surface, and wherein an inner surface of the inner set of voxels is adjacent to the outer surface of the target volume;

controlling the voxel set calculating module for providing a first frame description for an inner set of voxels, said first frame description reflecting criteria for the inner set of voxels;

controlling the voxel set calculating module for determining at least one outer set of voxels encompassing said target volume and said inner set of voxels, said at least one outer set of voxel being located outside said outer surface of the target volume and said inner set of voxels;

controlling the voxel set calculating module for providing a respective frame description for each outer set of voxels, each frame description reflecting criteria for the outer set of voxels; and controlling a calculation module to generate radiation dose profiles to be delivered to the target using said frame descriptions in the optimization problem that steers the delivered radiation.

18. A treatment planning computer structure for treatment planning in radiotherapy, wherein delivered radiation is determined using an optimization problem that steers the delivered radiation according to objectives reflecting criteria for regions of interest, that include at least one of: at least one target to be treated during treatment of a patient, organs at risk and/or healthy tissue, comprising:

a voxel set calculating module for calculating an inner set of voxels that encompasses an outer surface of a target volume and is outside the outer surface of the target volume based on a first frame description for an inner set of voxels, wherein an inner surface of the inner set of voxels is adjacent to the outer surface of the target volume, where the first frame description reflecting criteria for the inner set of voxels, and at least one outer set of voxels encompassing the target volume and the inner set of voxels and located outside said outer surface of the target volume and said inner set of voxels based on at frame description for outer set of voxels where each reflecting criteria for the outer set of voxels; and a calculation module configured for generating radiation dose profiles to be delivered to the target, for providing a convex optimization problem that steers the delivered radiation according to the objectives, and for calculating dose profiles for specific treatment configurations.

19. The treatment planning computer structure according to claim 18, further comprising:

a treatment plan module configured for creating treatment plans including determining the radiation dose profiles to be delivered during treatment based on the treatment configurations, wherein each radiation dose profile is modelled by a spatial dose volume distribution of radiation, a shape of the spatial distribution depending on the beam shape settings; and an optimizing module is configured for selecting an optimal treatment plan that satisfies the criteria.

20. The treatment planning computer structure according to claim 18, wherein the voxel set calculating module is configured to execute the steps of:

determining an inner set of voxels that encompasses the outer surface of a target volume;

providing a first frame description for an inner set of voxels, said first frame description reflecting at least one criterion for the inner set of voxels;

determining at least one outer set of voxels encompassing said target volume and said inner set of voxels;

providing a respective frame description for each outer set of voxels, each frame description reflecting at least one criterion for that outer set of voxels; and using said frame descriptions in the convex optimization problem that steers the delivered radiation.

21. A method for treatment planning for a radiotherapy, wherein delivered radiation is determined using an optimization problem that steers the delivered radiation according to objectives reflecting criteria for regions of interest, that include at least one of: at least one target to be treated during treatment of a patient, organs at risk and/or healthy tissue; said method comprising the steps of:

controlling a voxel set calculating module for determining an inner set of voxels that encompasses an outer surface of a target volume, wherein an inner surface of the inner set of voxels is adjacent to the outer surface of the target volume;

controlling the voxel set calculating module for providing a first frame description for an inner set of voxels, said first frame description reflecting at least one criterion for the inner set of voxels;

controlling the voxel set calculating module for determining at least one outer set of voxels encompassing said target volume and said inner set of voxels, said at least one outer set of voxels being located outside said outer surface of the target volume and said inner set of voxels;

controlling the voxel set calculating module for providing a respective frame description for each outer set of voxels, each frame description reflecting at least one criterion for that outer set of voxels; and controlling a calculation module to generate radiation dose profiles to be delivered to the target using said frame descriptions in the optimization problem that steers the delivered radiation.

* * * * *